United States Patent
Howard et al.

(10) Patent No.: US 11,653,847 B2
(45) Date of Patent: May 23, 2023

(54) METHOD AND APPARATUS FOR HYPERTENSION CLASSIFICATION

(71) Applicants: Newton Howard, Providence, RI (US); Mohamed Elgendi, Vancouver (CA); Yongbo Liang, Guangxi (CN); Zhencheng Chen, Guangxi (CN); Rabab Ward, Vancouver (CA)

(72) Inventors: Newton Howard, Providence, RI (US); Mohamed Elgendi, Vancouver (CA); Yongbo Liang, Guangxi (CN); Zhencheng Chen, Guangxi (CN); Rabab Ward, Vancouver (CA)

( * ) Notice: Subject to any disclaimer, the term of this patent is extended or adjusted under 35 U.S.C. 154(b) by 349 days.

(21) Appl. No.: 16/589,612

(22) Filed: Oct. 1, 2019

(65) Prior Publication Data
US 2020/0107737 A1    Apr. 9, 2020

Related U.S. Application Data

(60) Provisional application No. 62/740,578, filed on Oct. 3, 2018.

(51) Int. Cl.
*A61B 5/024* (2006.01)
*A61B 5/021* (2006.01)
*A61B 5/00* (2006.01)

(52) U.S. Cl.
CPC ...... *A61B 5/02427* (2013.01); *A61B 5/02116* (2013.01); *A61B 5/02125* (2013.01); *A61B 5/6826* (2013.01); *A61B 5/7221* (2013.01); *A61B 5/7239* (2013.01); *A61B 5/7264* (2013.01)

(58) Field of Classification Search
None
See application file for complete search history.

(56) References Cited

U.S. PATENT DOCUMENTS

| 2013/0018272 | A1* | 1/2013 | Hori | A61B 5/021 600/501 |
| 2017/0065230 | A1* | 3/2017 | Sinha | G16H 50/20 |

OTHER PUBLICATIONS

Liang, Yongbo, Chen, Zhencheng, Ward, Rabab, & Elgendi, Mohamed. (Sep. 2018). Hypertension Assessment via ECG and PPG Signals: An Evaluation Using MIMIC Database. Diagnostics. 8. 65. 10.3390/diagnostics8030065.

(Continued)

*Primary Examiner* — Yi-Shan Yang
(74) *Attorney, Agent, or Firm* — Michael Schwartz (57) ABSTRACT

A system for screening and management of hypertension, which includes a high precision fingertip photoplethysmography (PPG) acquisition device and the application software of hypertension screening and management in a portable device such as a smartphone. The former includes 905 nm wavelength infrared light emitting sensor, photoelectric receiving device, and Bluetooth transmission module. The latter includes PPG signal configuration and acquisition module, automatic hypertension classification and screening module and hypertension management module. The system can process the real-time PPG signal and can classify and evaluate the blood pressure level and carry on the long-term management and the hypertension health instruction.

7 Claims, 12 Drawing Sheets

| 701 | Obtain an original infrared PPG signal of the subject |
|---|---|
| 702 | Obtain a processed PPG signal by performing a signal conditioning of the original infrared PPG signal |
| 703 | Obtain a velocity of plethysmograph (VPG), acceleration of plethysmograph (APG), third derivative waveform (3rd Derivative) and fourth derivative waveform (4th Derivative) |
| 704 | Define and extract waveforms, from the processed PPG signal and its derivative waveforms |
| 705 | Analyze a physiological significance of the extracted waveforms; |
| 706 | Select at least one physiologically significant feature from the extracted waveforms, the at least one physiologically significant feature selected from a group including: |
| 707 | A slope from a first point of the processed PPG signal corresponding in time to a minimum of the APG waveform immediately preceding a systolic maximum of the PPG signal and a second point of the PPG signal corresponding in time to a maximum of the APG waveform immediately following the systolic maximum of the PPG signal, |
| 708 | A time interval from the systolic maximum of the PPG signal to the second point of the PPG signal, and |
| 709 | A time interval from the first point of the PPG signal to a third point of the PPG signal, the third point have an amplitude equal to the amplitude of the first point of the PPG signal; |
| 710 | Based on the selected at least one physiologically significant feature, establish a cubic Support Vector Machine (SVM) classification model of hypertension; and |
| 711 | Using the cubic Support Vector Machine (SVM) classification model of hypertension to generate classification of patients into different stages of hypertension. |

(56) References Cited

OTHER PUBLICATIONS

Liang, Yongbo, Chen, Zhencheng, Ward, Rabab, & Elgendi, Mohamed. (Dec. 2018). Hypertension Assessment Using Photoplethysmography: A Risk Stratification Approach. Journal of Clinical Medicine. 8.12. 10.3390/jcm8010012.

Elgendi, Mohamed. (Feb. 2012). On the Analysis of Fingertip Photoplethysmogram Signals. Current cardiology reviews 8.14-25. 10.2174/157340312801215782.

* cited by examiner

| 701 | Obtain an original infrared PPG signal of the subject |
|---|---|
| 702 | Obtain a processed PPG signal by performing a signal conditioning of the original infrared PPG signal |
| 703 | Obtain a velocity of plethysmograph (VPG), acceleration of plethysmograph (APG), third derivative waveform (3rd Derivative) and fourth derivative waveform (4th Derivative) |
| 704 | Define and extract waveforms, from the processed PPG signal and its derivative waveforms |
| 705 | Analyze a physiological significance of the extracted waveforms; |
| 706 | Select at least one physiologically significant feature from the extracted waveforms, the at least one physiologically significant feature selected from a group including: |
| 707 | A slope from a first point of the processed PPG signal corresponding in time to a minimum of the APG waveform immediately preceding a systolic maximum of the PPG signal and a second point of the PPG signal corresponding in time to a maximum of the APG waveform immediately following the systolic maximum of the PPG signal, |
| 708 | A time interval from the systolic maximum of the PPG signal to the second point of the PPG signal, and |
| 709 | A time interval from the first point of the PPG signal to a third point of the PPG signal, the third point have an amplitude equal to the amplitude of the first point of the PPG signal; |
| 710 | Based on the selected at least one physiologically significant feature, establish a cubic Support Vector Machine (SVM) classification model of hypertension; and |
| 711 | Using the cubic Support Vector Machine (SVM) classification model of hypertension to generate classification of patients into different stages of hypertension. |

Fig. 7

METHOD AND APPARATUS FOR HYPERTENSION CLASSIFICATION

BACKGROUND

Field of the Invention

The present invention relates to medical and health equipment and a method for screening and management of hypertension, which can be used for the screening and evaluation of hypertension for individuals or family and for the management and guidance of different stage hypertension.

Description of the Related Art

As an important physiological index of the cardiovascular system, blood pressure (BP) plays an important role in predicting the occurrence of acute and chronic cardiovascular diseases (CVDs). Therefore, the early screening and evaluation of patients with hypertension (HT) or prehypertension are of great practical significance. At present, the blood pressure measurement uses the cuff mercury or electronic sphygmomanometer. This measurement method has been widely recognized and popularized after hundred years of development, and it has played a major role in the control of CVDs. However, both the Korotkoff Sound method and the Oscillometric method need to use cuff and pressure to the forearm when the blood pressure is measured. The measurement is very easily affected by the operation and use conditions, such as the operation of the cuff, sitting posture, exercise and so on. In addition, it also has a certain white coat phenomenon for some patients. Therefore, its role has been greatly limited in current severe CVDs prevention and control situation. The cuff-less hypertension screening technology and blood pressure detection technology in the new situation of cardiovascular health management is forming an urgent need. At present, with the increasing demand for personal health equipment, more and more health information measuring or evaluating equipment and systems are being researched and developed.

Photoplethysmography (PPG) contains very abundant physiological information about the operation of the cardiovascular circulation system, and it has the characteristics of low-cost and convenient signal acquisition. It is therefore widely concerned by researchers, and a series of investigations and research are carried out in-depth. A PPG signal is extracted by the use of (1) an LED transmit section to generate the red or infrared light to illuminate the skin of a fingertip, earlobe or forehead and (2) a photosensitive diode to measure the time-varying light absorption by the tissue which can reflect the changes in the blood volume. The common PPG acquisition methods are divided into transmission and reflection. Therefore, it is the external manifestation and aggregated expression of many physiological processes in the cardiovascular circulation system. The PPG signal is a high fusion signal which covers the activity of heart's systolic and diastolic period, hemodynamic, hemorheology and network information of human peripheral microcirculation system.

The present invention is based on PPG morphological theory, quantitatively analyses the characteristic of PPG, establishes the intrinsic relation between PPG characteristic and cardiovascular cycle physiology process, and realizes the accurate classification and early screening of hypertension.

SUMMARY

The technical problem to be solved by the invention is to provide non-invasive, convenient, accurate and reliable evaluation and screening methods of hypertension and its measuring instruments. The method requires less input signal, the relationship between input signal and blood pressure level is stable. The measuring instrument also has the characteristics of small size, simple operation, inexpensive price, and suitability for personal and family use. In order to solve the technical problem, the specific technical plan of the invention is as follows.

The system of the present invention to provide the real-time evaluation and screening of hypertension includes a PPG acquisition probe, a portable computing device (such as a smartphone) in wireless communication with the acquisition probe and executing application software to execute the inventive functions described herein, and storage space in a cloud-based server computer.

The PPG acquisition probe includes a sequential connection three-channel PPG photoelectric module, a signal conditioning module, an operational processing module, an external mass storage module, a voice guide and broadcast module, and a wireless communication module.

The three-channel PPG photoelectric module includes an infrared photoelectric emitting and receiving module located in the front, middle, and root sections of the PPG acquisition probe, wherein the three sections are spaced apart by 10 mm, respectively.

The output of the operation module is connected to an external mass storage module, a voice guide and broadcast module, and a wireless communication module, respectively.

The signal conditioning module comprises a two-stage amplifying circuit, a bandpass filter circuit and a baseline drift suppression circuit, which is used to amplify, filter and signal conditioning the faint PPG signal, and its output connects to the operational process module.

The operational process module performs the functions of PPG acquisition, three-channel photoelectric module function evaluation and selection, data compression and transmission, etc.

The external mass storage module includes the data of the operation result, the photoelectric working mode and other information storage.

The wireless communication module includes receiving commands and sending data to achieve information interaction with the application software in the portable device.

Furthermore, a method of the present invention for real-time evaluation and screening of hypertension using a fingertip photoplethysmograph (PPG) signal includes the following steps:

a. Obtain an original infrared PPG signal of the subject;
b. Obtain a high-quality PPG signal after signal conditioning and signal quality evaluation;
c. Obtain velocity of plethysmograph (VPG), acceleration of plethysmograph (APG), third derivative waveform ($3^{rd}$ Derivative) and fourth derivative waveform ($4^{th}$ Derivative) through four times differential process using the processed PPG signal;
d. Based on the PPG signal and its derivative waves, the waveform characteristics are defined and extracted, which can include time interval, amplitude, area, ratio, slope, energy parameter and so on. The physiological significance of PPG features is analyzed, and the top three optimal features are selected;

e. Based on the above selected feature, the classification model of hypertension is established, and the evaluation and screening of hypertension based on the morphological characteristics of the PPG signal are realized.

After signal processing and signal quality evaluation, the raw PPG signal obtained by the acquisition probe will be transferred to the application software in the portable device through the wireless transmission module, wherein, the acquisition probe set up three pairs of infrared transmission photoelectric module distributed in the front, middle, root of the acquisition probe.

Firstly, the signal quality of PPG waveform acquired from different photoelectric modules is compared and the photoelectric module which produces the optimal signal quality is selected as the working module of subsequent signal acquisition. The setting of three photoelectric modules is mainly used to solve the poor PPG signal caused by the different peripheral circulatory system condition which is different because of gender, age, blood perfusion and other factors.

The application software executing on the portable device can display the received PPG signal in real time. The PPG signal is processed as 0.5 hz-8 hz bandpass filtering and then its derivative waveforms are acquired as the forward difference process. The PPG, VPG, APG, 3rd Derivative and 4th Derivative waves are used to obtain the PPG features.

Based on these features, the cubic Support Vector Machine (SVM) blood pressure classification model is established, and the evaluation of blood pressure level and the screening of hypertension are realized, and the results of blood pressure level can be displayed in real-time in the application software.

PPG signal data, its features, and evaluation of blood pressure level can be stored in the user-specific cloud space, for long-term blood pressure level management and health guidance. Compared with the existing technology, the instrument is portable and convenient for the family and community health care use and provides important reference physiological information for the early prevention of hypertension. At the same time, the instrument is easy to operate and only needs to hold the fingertip to collect PPG signal in order to realize the evaluation of blood pressure level and classification of hypertension. In addition, it reduces the pain and the psychological burden of diagnosis and detection.

BRIEF DESCRIPTION OF THE DRAWING

The disclosure may be more completely understood in consideration of the detailed description of various embodiments of the disclosure that follows in connection with the accompanying drawings, in which:

FIGS. 6.A through 6.C show the scatter between systolic blood pressure and PPG feature, wherein FIG. 6.A shows slope of b*c* vs SBP, FIG. 6.B shows Sc* interval vs SBP, and FIG. 6.C shows b*b2 interval vs SBP.

FIG. 7 illustrates a flowchart of PPG signal processing and hypertension evaluation that are conducted in the hardware device and matching app.

DETAILED DESCRIPTION OF THE PREFERRED EMBODIMENT

The system and method of hypertension screening and classification disclosed in the preferred embodiment of the present invention can be used to evaluate blood pressure level and to screen for hypertension. It can also be used to evaluate vascular health, such as vascular aging, arteriosclerosis, and vascular compliance. The following illustrates the specific realization of the measurement method.

Figure 1:
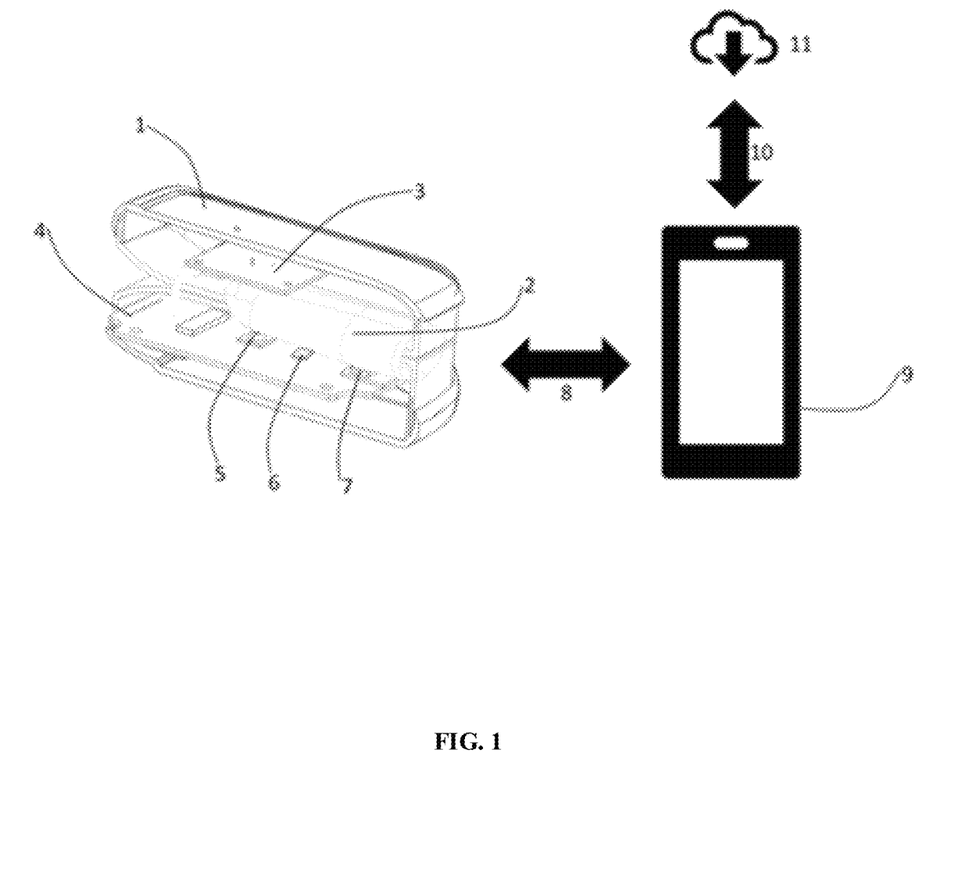
FIG. 1 depicts a diagram of a preferred embodiment of the hypertension evaluation system that can capture photoplethysmograph (PPG) signals and conduct the hypertension evaluation.
Figure 2:
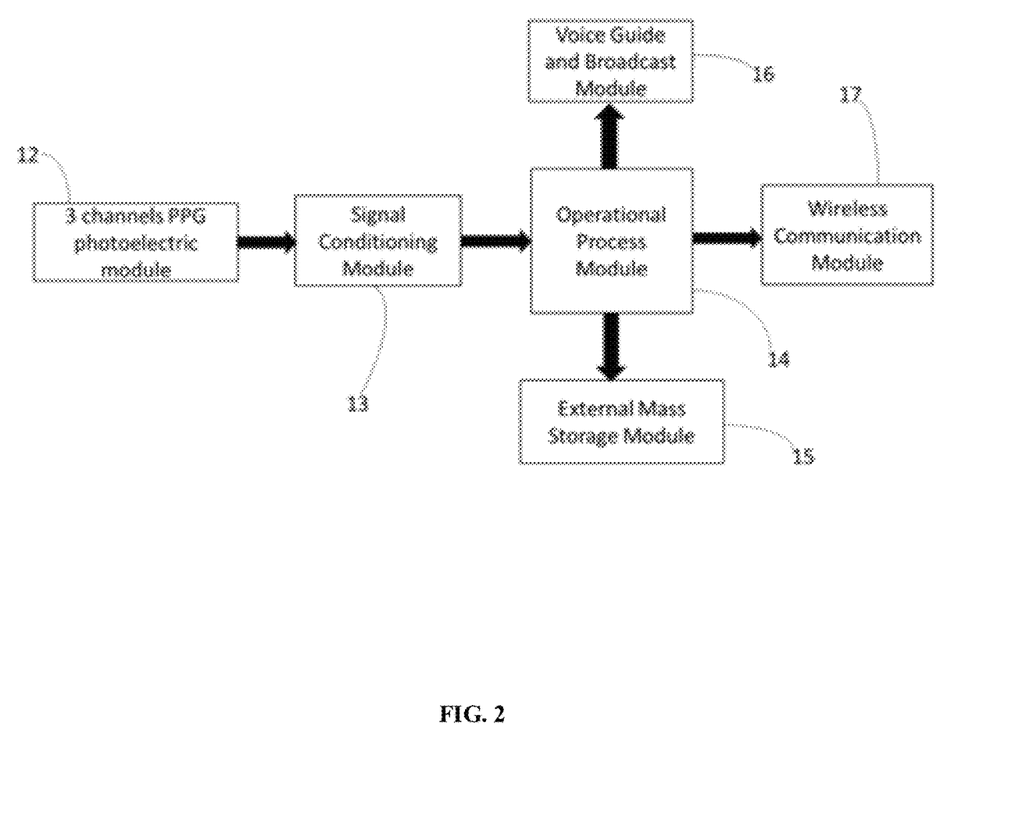
FIG. 2 depicts a functional block diagram of a preferred embodiment PPG acquisition probe implemented by the system of FIG. 1 that can capture PPG signals and transmit the PPG data to a portable device for processing and evaluation.

FIG. 1 is an overall block diagram of the preferred embodiment hypertension evaluation system of the present invention. The system shown in FIG. 1 includes a PPG acquisition probe 1, which is wirelessly connected 8 to a portable device 9 such as a smartphone or the like. The portable device 9 is also shown interconnected through a network connection 10 to a cloud-based server computer 11 that provides for data storage, archival and retrieval. FIG. 2 shows a functional block diagram of the PPG acquisition probe 1, which includes a three-channel PPG photoelectric module 12, a signal conditioning module 13, an operational process module 14, an external mass storage module 15, a wireless communication module 17, and a voice guide and broadcast module 16. Also described (not shown) are a real-time waveform display module in the application software of the portable device 9, a PPG acquisition probe function configuration module, a hypertension classification and screening module, and a hypertension management and health guidance module.

The PPG photoelectric module 12, signal conditioning module 13, and operational process module 14 are interconnected to complete the PPG signal acquisition. The operational process module 14 includes sequential execution of PPG signal acquisition, three-channel photoelectric module function evaluation and selection, data compression, and data transmission. The output of the operational process module 14 respectively connects the external mass storage module 15, the wireless communication module 17, and the voice guidance and broadcast module 16, which together realize the storage, communication and voice guidance function of the PPG signals and partial result, respectively.

The system of the present invention operates as follows. Because the human finger will have different traits due to sex, age, blood overall volume, skin roughness and other factors, the probe 1 is designed as three infrared photoelectric transmission and receiving pathways in the front 7, middle 6 and root 5 of the probe groove. Infrared light is emitted by an IR tube 3, which shines on the human finger when inserted into the probe 1. The blood of the human finger can absorb part of infrared light, and the effect of the heart's periodic beat makes the light absorption process periodic. This periodic change process is converted by the photoelectric receiving tube into an electrical signal to form the original faint PPG signal. In addition, the instrument conducts the PPG signal quality evaluation under the three different photoelectric modules at first. The photoelectric module that acquires the best signal quality is selected as a working photoelectric module, and then the other two photoelectric modules are closed.

The PPG signal obtained by the photoelectric module is very weak and is accompanied with a lot of interference signals; it therefore must be amplified, filtered and disturbed. The raw PPG signal is amplified by an amplification circuit and then passed through a 0.5 hz-12 hz bandpass filter to obtain a smooth and effective PPG signal. For the processed PPG signal, the digital conversion of the signal is carried out through an A/D converter inside the operational process module 14, and the data is encoded and compressed through a microprogrammed control unit (MCU, not shown). The compressed data 8 is sent to the portable device 9 through the wireless communication module 17. In the process, partial configuration information and temporary calculation results are stored in the external mass storage module 15.

The real-time PPG signal data received by the portable device 9, after further denoising and optimized processing, is carried on the multiple forward difference operation to obtain VPG, APG, $3^{rd}$ Derivative and $4^{th}$ Derivative wave. A lot of PPG features are defined and extracted based on the PPG and its derivative waveforms. The top three optimal features, which are slope of b*c*, Sc* interval and b*b2 interval, are selected. The cubic SVM model is established and used to classify and screen hypertension using these features. The result is shown in the display of the portable device 9 and uploaded to the user-specific cloud storage server computer 11 via the internet.

The hypertension classification and screening module is the core module of the whole system, responsible for including data analysis and model establishment, the results of storage and real-time display control, and more importantly, PPG characteristic waves recognition and features extraction, data classification model implementation. The operation process mainly includes the following steps:

(a) After filtering and the differential process of the PPG signal, the smooth PPG and VPG, APG, 3rd Derivative, 4th Derivative waveforms are obtained.

(b) The features defined based on the PPG and its derivative waves include time span, amplitude, area, ratio, slope and so on. These features show different states according to different blood pressure levels and have a good quantitative expression of blood pressure, and they are related to the formation process of systolic pressure in arterial blood pressure.

(c) The systolic blood pressure (SBP) of the human arterial pressure is the maximum value formed the in the middle of the systolic period under the action of the propulsion and reflection fusion of the blood from the heart. Therefore, the propulsion and reflection fusion process of the blood in the arteries during the systolic period plays an important role in the formation of SBP. The PPG signal reflects the physical changes of blood volume in the blood vessel during cardiac activity and blood transmission, and it is the direct show of blood volume state. The VPG signal reflects the blood volume change extent in the peripheral blood vessels, and it is the manifestation of the blood change. The APG signal reflects the ability of the speed change for the blood volume, and this ability largely reflects the systolic and diastolic ability of the heart. The features of strong correlation with systolic pressure and greater contribution weight are with BP label concentrated in the position of systolic wave and reflection wave, specifically in the interval between b wave and c wave. We find that some features reflect the details of the fusion process of the main propulsion wave and the reflected wave such as slope of b*c*, Sc* interval, and b*b2 interval. FIG. 5 shows four subjects' PPG and their derivatives, and the four subjects have different blood pressure levels and represent normal (graph A), prehypertension graph B), stage 1 hypertension (graph C) and stage 2 hypertension (graph D), respectively. In these graphs we find that systolic peak and tidal wave have different fusion in different blood pressure stage. This different fusion has generality and some features in this period (b*--c* period) have strong correlation with SBP.

Figure 6:
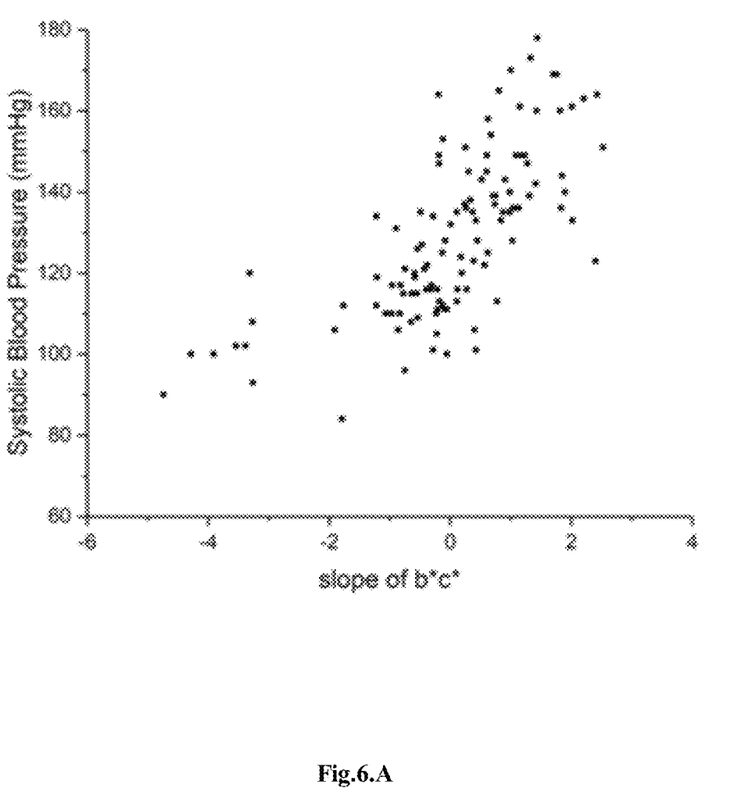
Figure 6C:
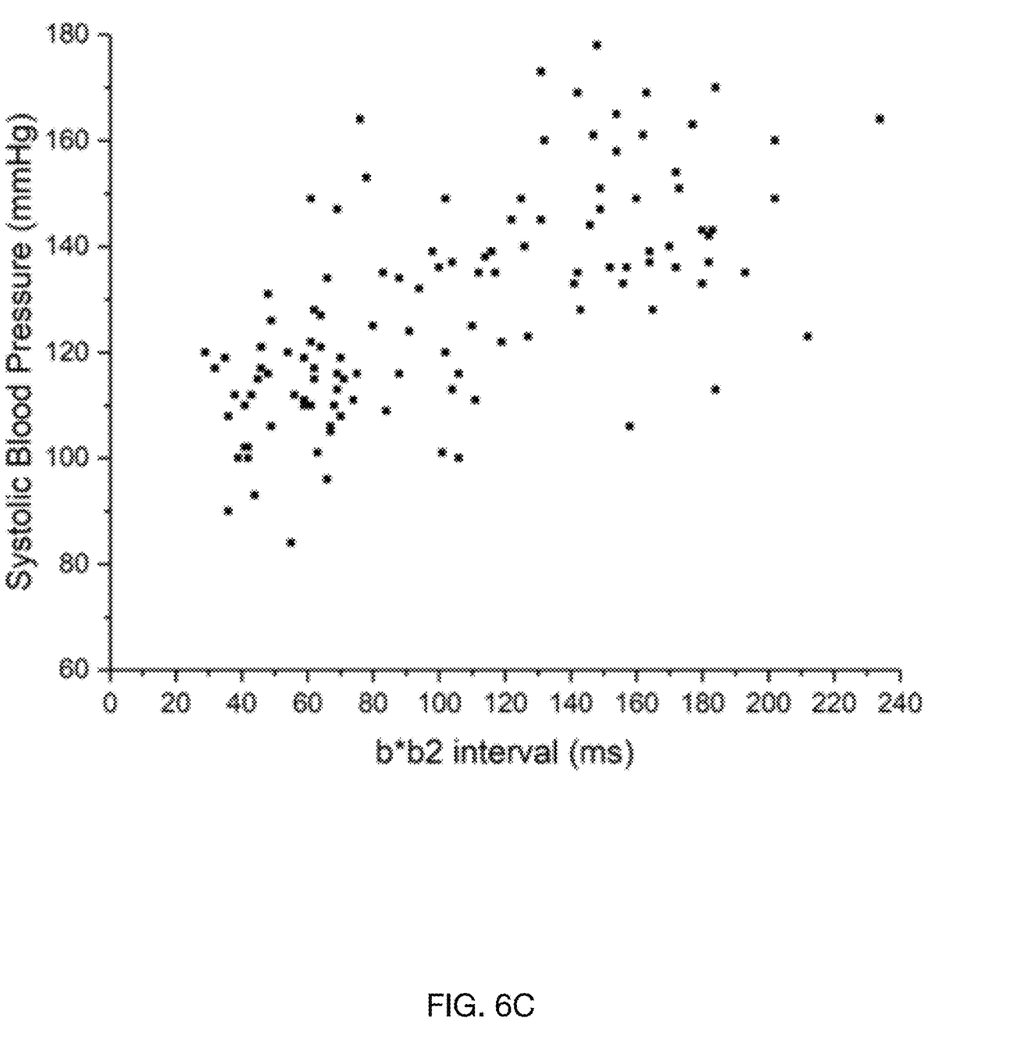

(d) The features have a good expression for the condition of main propulsion wave and reflected wave. FIG. 6.A, FIG. 6.B and FIG. 6.C show the scatter figures between SBP and slope $b_{-2}c_{-2}$, Sc* interval and b*b2 interval respectively and the spearman correlation coefficients are 0.73, 0.71, 0.66 respectively.

(e) The hypertension classification model is established based on the Cubic SVM. The F1 score of the model is shown in Table 1 below.

An exemplary flow diagram of an embodiment of PPG signal processing and hypertension evaluation is shown in FIG. 7. As shown in FIG. 7, the steps may include:

701: obtaining an original infrared PPG signal of the subject using a fingertip photoplethysmograph (PPG);

702: obtaining a processed PPG signal by performing a signal conditioning of the original infrared PPG signal using an amplifying circuit, a bandpass filter circuit and a baseline drift suppression circuit;

703: obtaining derivative waveforms of the processed PPG signal including a velocity of plethysmograph (VPG), acceleration of plethysmograph (APG), third derivative waveform (3rd Derivative) and fourth derivative waveform (4th Derivative) through a four times differential process using the processed PPG signal;

704: defining and extracting waveforms, from the processed PPG signal and its derivative waveforms, the extracted waveforms comprising at least a time interval, an amplitude, an area, a ratio, a slope, and an energy parameter;

705: analyzing a physiological significance of the extracted waveforms;

706: selecting at least one physiologically significant feature from the extracted waveforms, the at least one physiologically significant feature selected from a group including:

707: a slope from a first point of the processed PPG signal corresponding in time to a minimum of the APG waveform immediately preceding a systolic maximum of the PPG signal and a second point of the PPG signal corresponding in time to a maximum of the APG waveform immediately following the systolic maximum of the PPG signal,

708: a time interval from the systolic maximum of the PPG signal to the second point of the PPG signal, and

709: a time interval from the first point of the PPG signal to a third point of the PPG signal, the third point have an amplitude equal to the amplitude of the first point of the PPG signal;

710: based on the selected at least one physiologically significant feature, establishing a cubic Support Vector Machine (SVM) classification model of hypertension; and 711: using the cubic Support Vector Machine (SVM) classification model of hypertension to generate classification of patients into different stages of hypertension.

TABLE 1

Classification Result of Normal Group and Hypertension Group

| | F1 Score |
|---|---|
| Normal vs. Prehypertension | 0.72 |
| Normal vs. Stage 1 Hypertension | 0.8421 |
| Normal vs. Stage 2 Hypertension | 0.9286 |
| Normal vs. Hypertension | 0.8955 |
| Normal + Prehypertension vs. Hypertension | 0.6984 |

Figure 3:
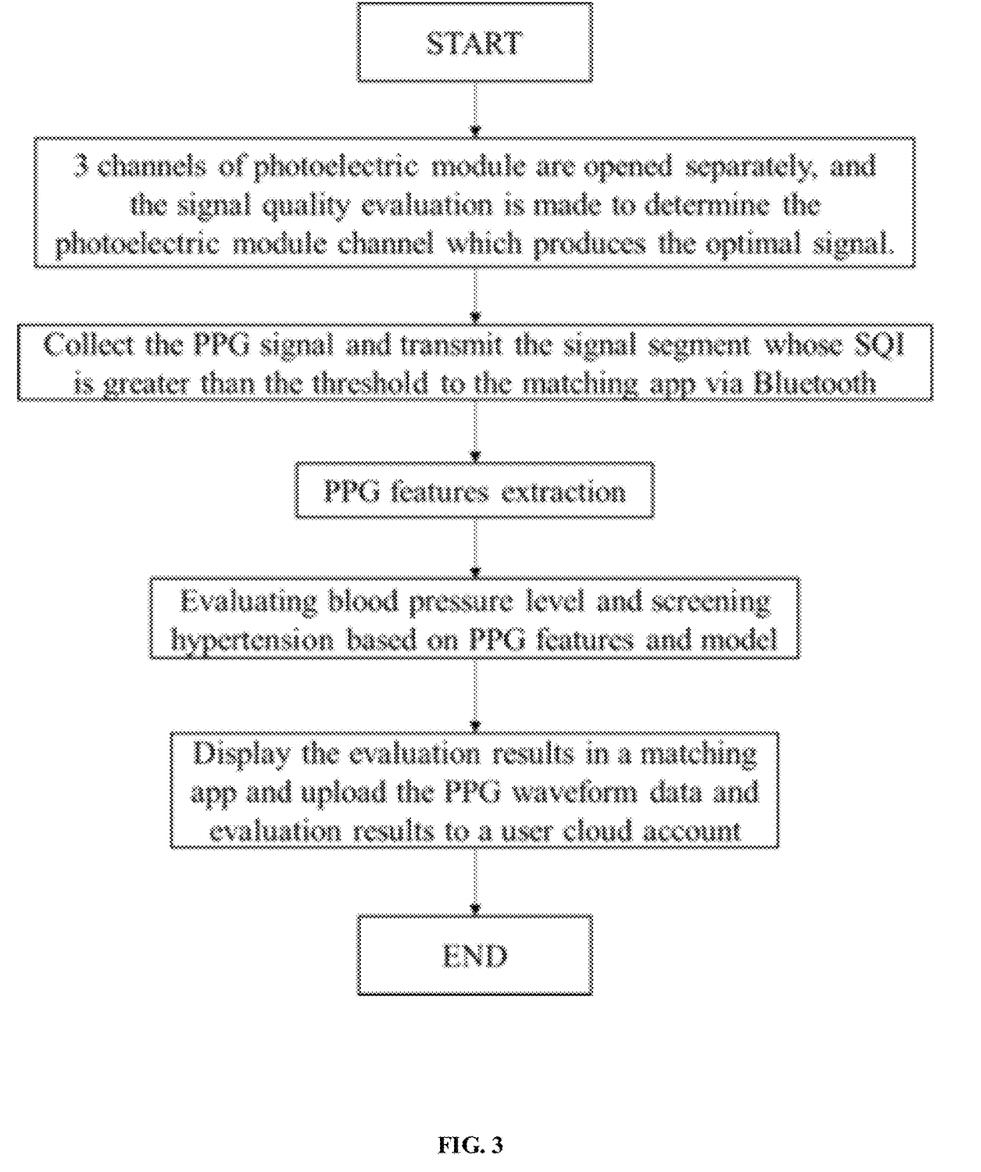
FIG. 3 illustrates a preferred embodiment flowchart of the overall operation of the PPG signal processing and hypertension evaluation that are conducted in the portable device and matching application.
Figure 4:
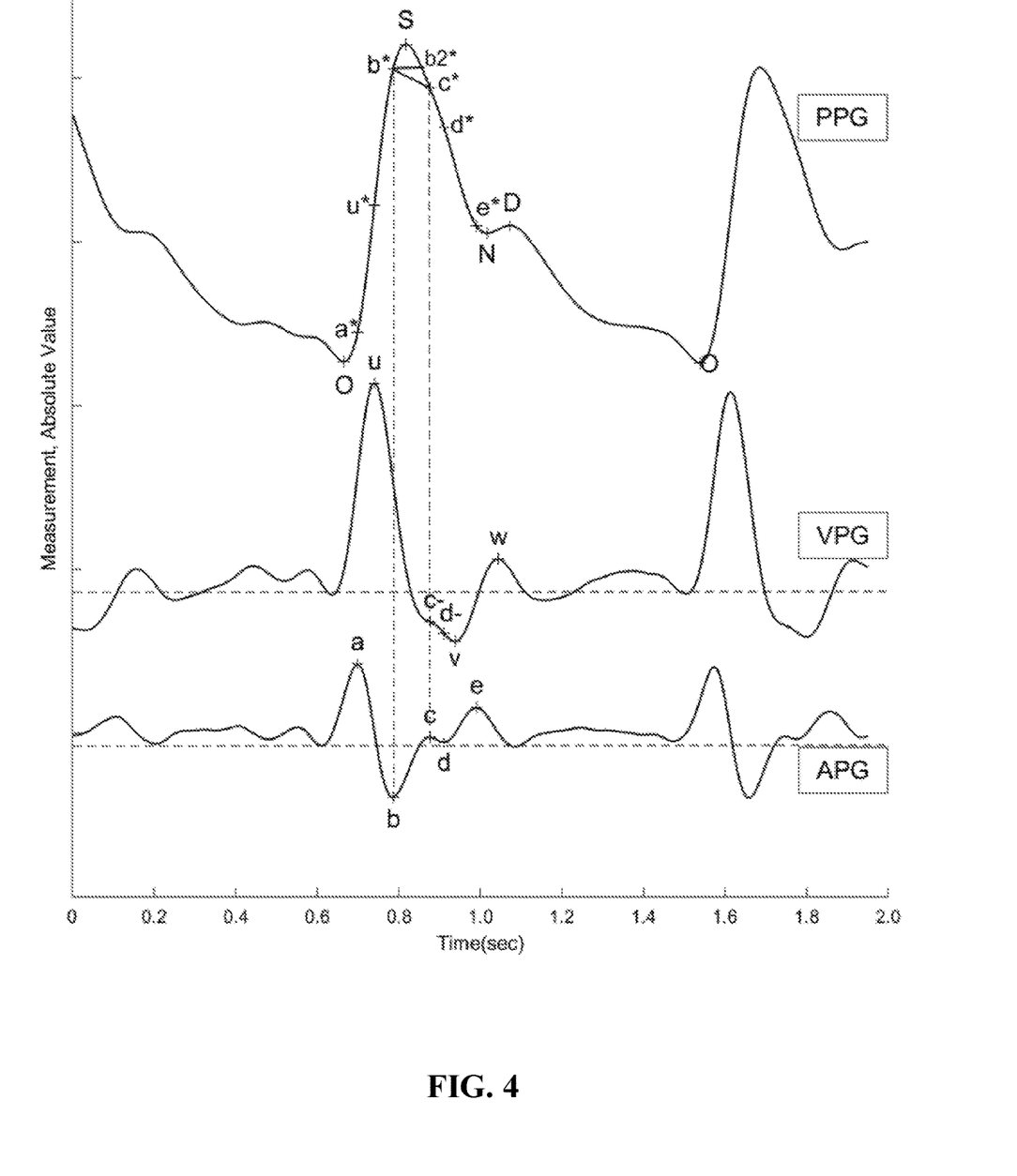
FIG. 4 depicts the definition of the PPG waveform, its derivatives and the PPG features.
Figure 5A:
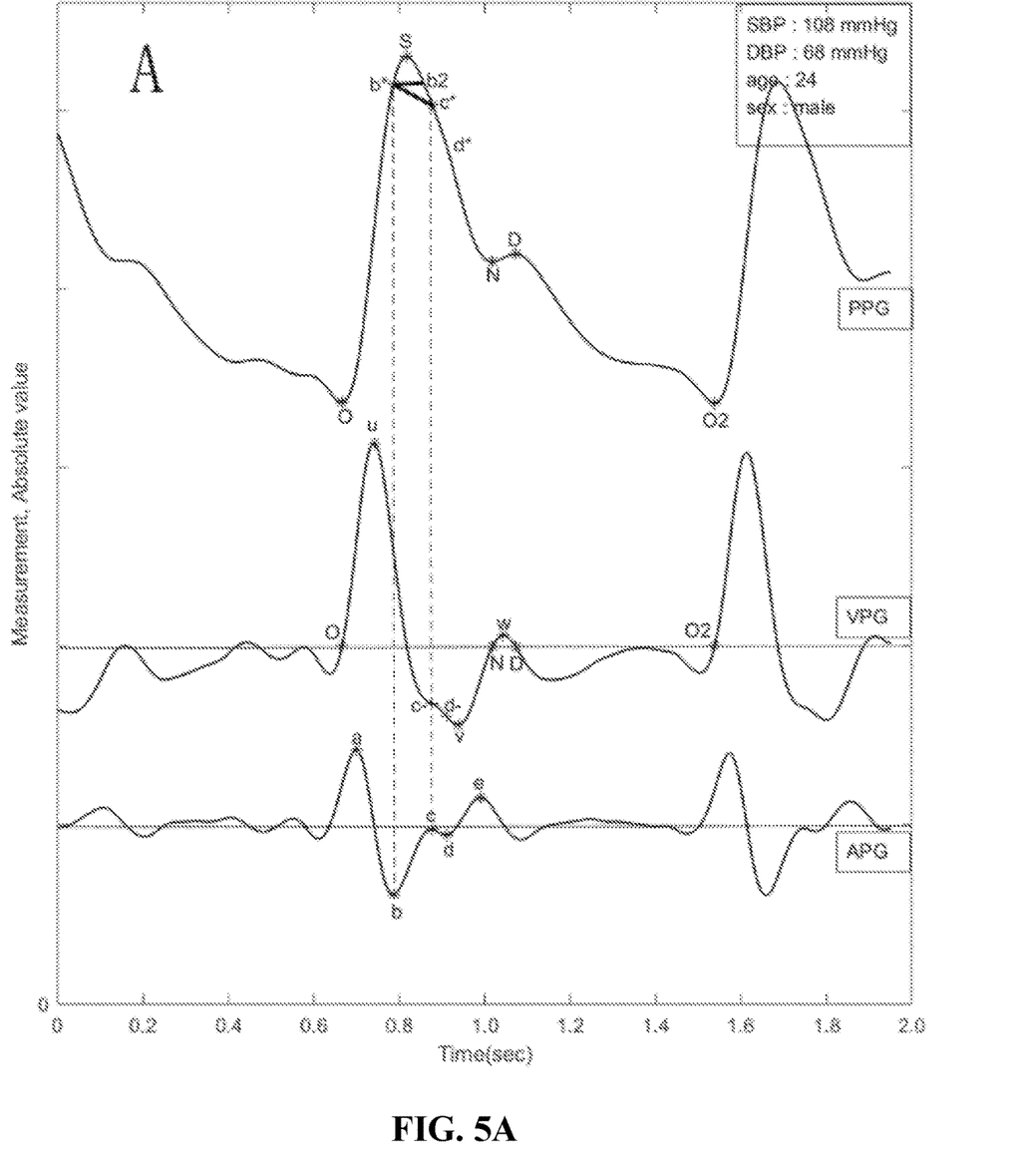
FIG. 5 shows the different waveform and feature in normal (A), prehypertension (B), stage 1 hypertension (C) and stage 2 hypertension (D).
Figure 5B:
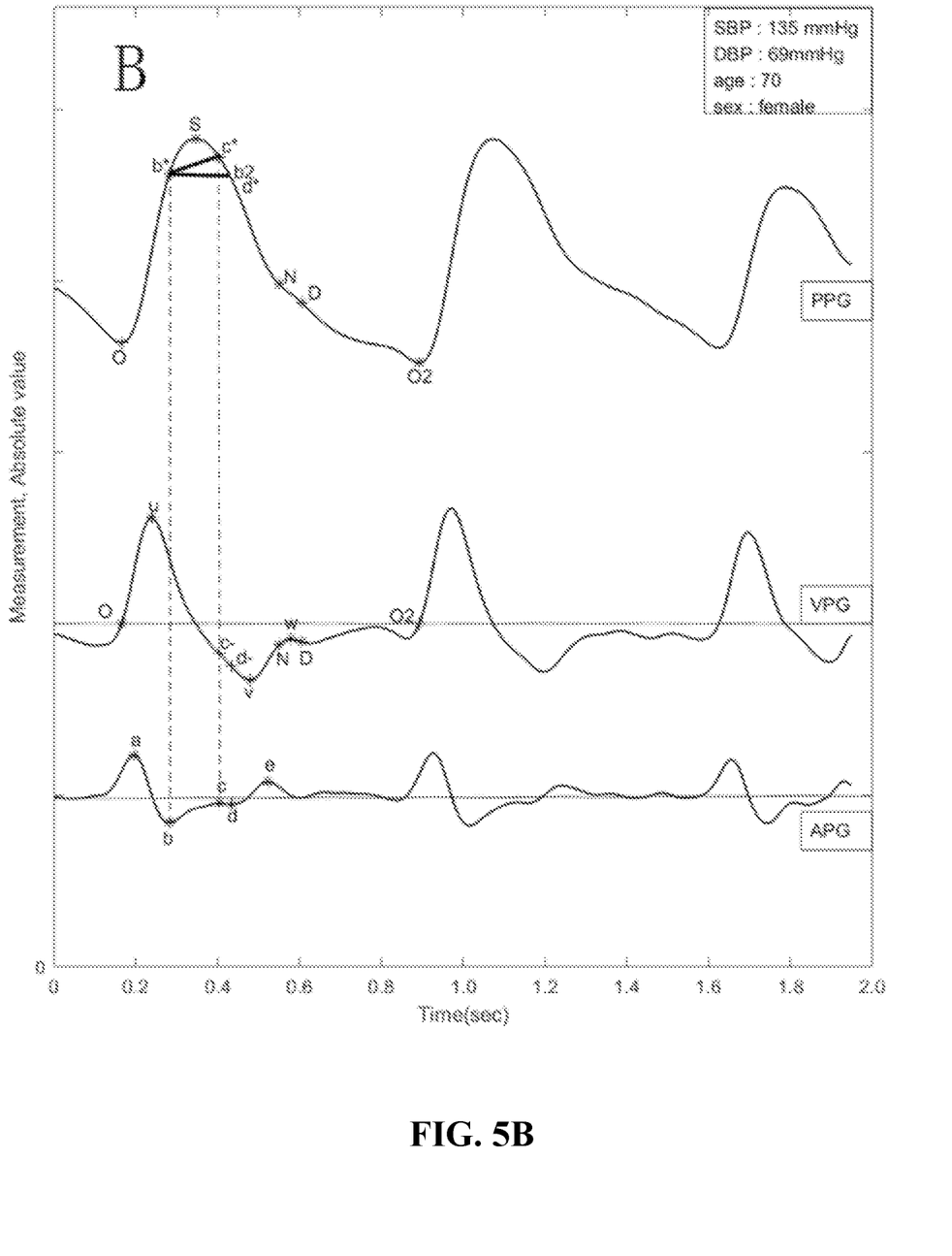
Figure 5C:
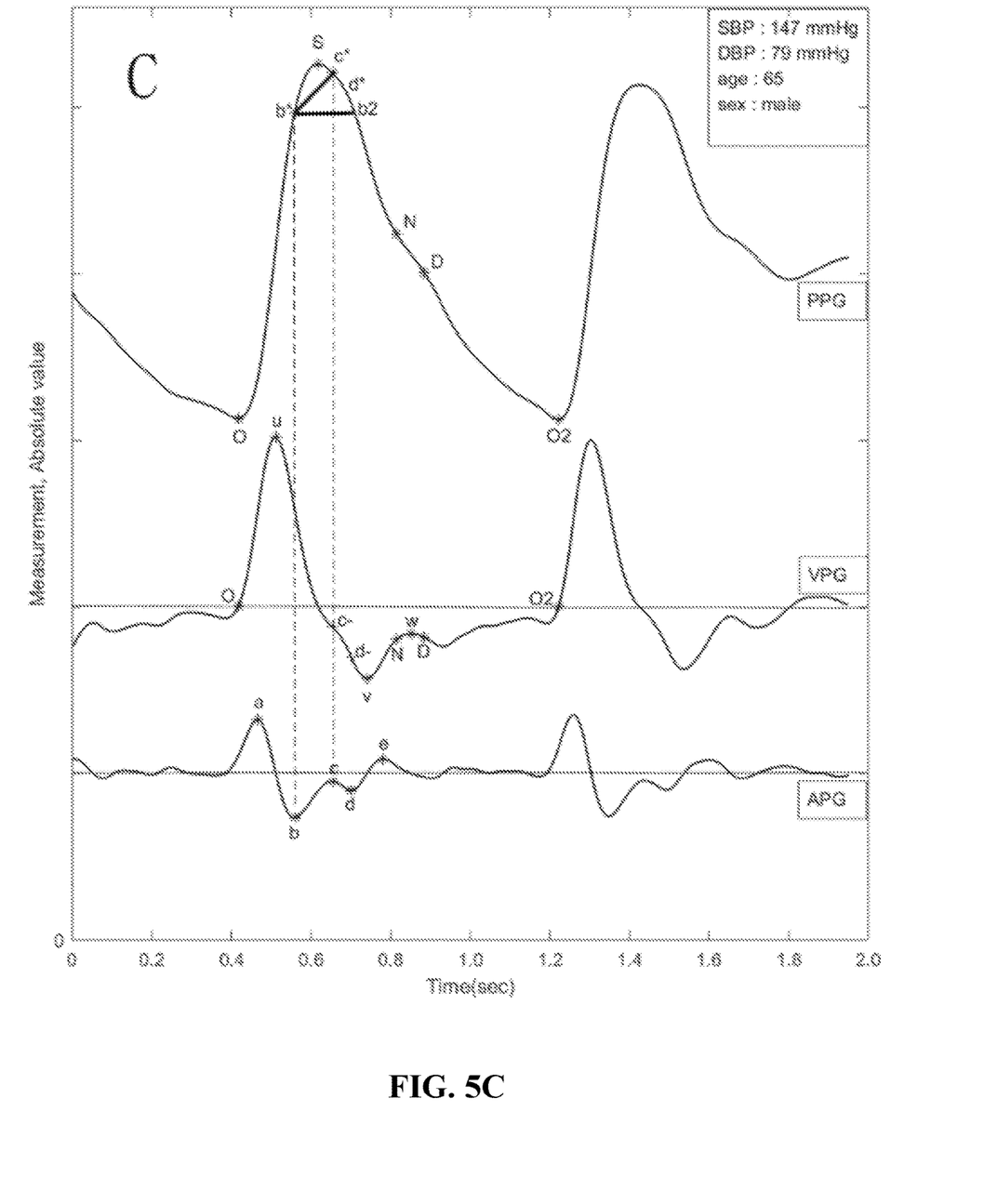
Figure 5D:
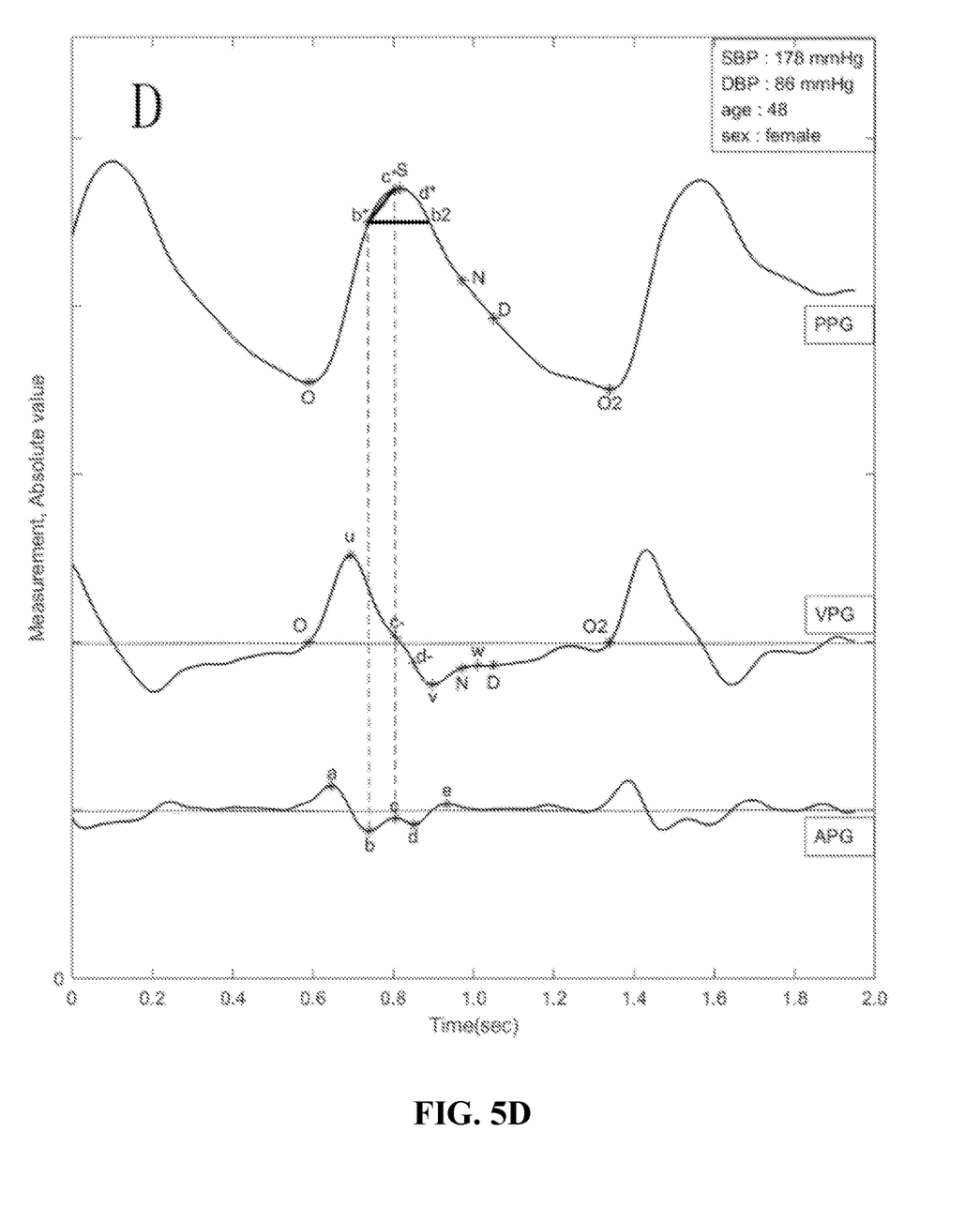

With reference to the flowchart of FIG. 3, the preferred embodiment method of the present invention for real-time evaluation and screening of hypertension using a fingertip photoplethysmograph (PPG) signal includes the following steps. First, three channels of the photoelectric module are opened separately, and the signal quality evaluation is made to determine the photoelectric module channel which produces the optimal signal. Then, collect the PPG signal and transmit the signal segment whose SQI is greater than the threshold to the matching app via wireless (Bluetooth). Next, PPG features are extracted, and at step 308 evaluation of blood pressure level and screening hypertension based on PPG features and model. Finally, the evaluation results are displayed in a matching application on the portable device, uploading the PPG waveform data and evaluation results to a user cloud account at the server.

What is claimed is:

1. A system for real-time evaluation and screening of hypertension of a subject, the system comprising a processor and storage storing data and software for performing a method comprising the steps of:
   a) obtaining an original infrared PPG signal of the subject using a fingertip photoplethysmograph (PPG);
   b) obtaining a processed PPG signal by performing a signal conditioning of the original infrared PPG signal using an amplifying circuit, a bandpass filter circuit and a baseline drift suppression circuit;
   c) obtaining derivative waveforms of the processed PPG signal including a velocity of plethysmograph (VPG) and an acceleration of plethysmograph (APG) from the processed PPG signal;
   d) defining and extracting waveforms, from the processed PPG signal and its derivative waveforms, the extracted waveforms comprising at least a time interval, an amplitude, an area, a ratio, a slope, and an energy parameter;
   e) analyzing a physiological significance of the extracted waveforms to obtain at least one physiologically significant feature;
   f) selecting the at least one physiologically significant feature from the extracted waveforms, the at least one physiologically significant feature selected from a group including:
      i. a slope from a first point of the processed PPG signal corresponding in time to a minimum of the APG waveform immediately preceding a systolic maximum of the processed PPG signal and a second point of the processed PPG signal corresponding in time to a maximum of the APG waveform immediately following the systolic maximum of the processed PPG signal,
      ii. a time interval from the systolic maximum of the processed PPG signal to the second point of the processed PPG signal, and
      iii. a time interval from the first point of the processed PPG signal to a third point of the processed PPG signal, the third point have an amplitude equal to the amplitude of the first point of the processed PPG signal;
   g) based on the selected at least one physiologically significant feature, establishing a cubic Support Vector Machine (SVM) classification model of hypertension; and
   (h) using the cubic Support Vector Machine (SVM) classification model of hypertension to generate classification of patients into different stages of hypertension.

2. The system of claim 1 further comprising obtaining a third derivative waveform (3rd Derivative) and fourth derivative waveform (4th Derivative) that are obtained through a four times differential process performed on the processed PPG signal.

3. A method for real-time evaluation and screening of hypertension of a subject to be performed in a system comprising a processor and storage storing data and software, comprising the steps of:
   obtaining an original infrared PPG signal of the subject using a fingertip photoplethysmograph (PPG);
   obtaining a plurality of derivative waveforms as a function of the PPG signal, including at least a velocity of plethysmograph (VPG) waveform and an acceleration of plethysmograph (APG) waveform;
   defining and extracting a plurality of waveforms from the PPG signal and its derivative waveforms;
   analyzing a physiological significance of the extracted plurality of waveforms to obtain at least one physiologically significant feature;
   selecting the at least one physiologically significant feature from the extracted waveforms, the at least one physiologically significant feature selected from a group including:
      i. a slope from a first point of the PPG signal corresponding in time to a minimum of the APG waveform immediately preceding a systolic maximum of the PPG signal and a second point of the PPG signal corresponding in time to a maximum of the APG waveform immediately following the systolic maximum of the PPG signal,
      ii. a time interval from the systolic maximum of the PPG signal to the second point of the PPG signal, and
      iii. a time interval from the first point of the PPG signal to a third point of the PPG signal, the third point have an amplitude equal to the amplitude of the first point of the PPG signal; and
   based on the selected at least one physiologically significant feature, establishing a cubic Support Vector Machine (SVM) classification model of hypertension; and
   using the cubic SVM classification model of hypertension to generate classification of patients into different stages of hypertension.

4. The method of claim 3 further comprising the step of obtaining a processed PPG signal by performing a signal conditioning and a signal quality evaluation of the original infrared PPG signal of the subject using an amplifying circuit, a bandpass filter circuit and a baseline drift suppression circuit.

5. The method of claim 4 wherein the plurality of derivative waveforms further comprises
a third derivative waveform (3rd Derivative) and fourth derivative waveform (4th Derivative) that are obtained through a four times differential process performed on the PPG signal.

6. The method of claim 5 wherein the plurality of extracted waveforms comprises at least a time interval, an amplitude, an area, a ratio, a slope, and an energy parameter.

7. The method of claim 3, wherein the plurality of extracted waveforms comprises at least a time interval, an amplitude, an area, a ratio, a slope, and an energy parameter.

* * * * *